United States Patent
Zhang et al.

(10) Patent No.: US 8,679,024 B2
(45) Date of Patent: Mar. 25, 2014

(54) SYSTEM AND METHOD FOR DERIVING RESPIRATION FROM INTRACARDIAC ELECTROGRAMS (EGM) OR ECG SIGNALS

(75) Inventors: Xusheng Zhang, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 12/912,217

(22) Filed: Oct. 26, 2010

(65) Prior Publication Data

US 2012/0101393 A1    Apr. 26, 2012

(51) Int. Cl.
A61B 5/08    (2006.01)
A61B 5/02    (2006.01)

(52) U.S. Cl.
USPC .......................... 600/484; 600/481

(58) Field of Classification Search
USPC ................. 600/481–508, 529–543
See application file for complete search history.

(56) References Cited

U.S. PATENT DOCUMENTS

| | | |
|---|---|---|
| 4,576,179 A | 3/1986 | Manus |
| 4,580,575 A | 4/1986 | Birnbaum |
| 4,757,824 A | 7/1988 | Chaumet |
| 5,105,354 A | 4/1992 | Nishimura |
| 5,170,794 A | 12/1992 | Reiche |
| 6,449,509 B1 * | 9/2002 | Park et al. ............... 607/20 |
| 7,361,146 B1 * | 4/2008 | Bharmi et al. ........... 600/484 |
| 7,524,292 B2 | 4/2009 | Cho |
| 7,733,224 B2 | 6/2010 | Tran |
| 2005/0085738 A1 * | 4/2005 | Stahmann et al. ....... 600/529 |
| 2005/0148895 A1 * | 7/2005 | Misczynski et al. ..... 600/513 |
| 2005/0256419 A1 | 11/2005 | Roach |
| 2006/0094967 A1 | 5/2006 | Bennett |
| 2007/0032733 A1 | 2/2007 | Burton |
| 2008/0119747 A1 | 5/2008 | Mietus |
| 2008/0119749 A1 * | 5/2008 | Haro et al. ............... 600/528 |
| 2008/0319326 A1 * | 12/2008 | Behbehani et al. ...... 600/484 |
| 2009/0227877 A1 | 9/2009 | Tran |

OTHER PUBLICATIONS (PCT/US2011/057473) PCT Notification of Transmittal of the International Search Report and the Written Opinion of the International Searching Authority.

* cited by examiner

*Primary Examiner* — Patricia Mallari
*Assistant Examiner* — Tiffany Weston
(74) *Attorney, Agent, or Firm* — Michael C. Soldner

(57) ABSTRACT

A method and apparatus for monitoring respiration in a patient sense a cardiac electrical signal and detect signal peaks from the cardiac electrical signal. A peak amplitude waveform is generated from the signal peaks. a first derivative of the peak amplitude waveform is computed. Inspiration pulses are derived from the first derivative signal, and a respiration metric can be computed using the inspiration pulses derived from the cardiac electrical signal.

14 Claims, 5 Drawing Sheets

SYSTEM AND METHOD FOR DERIVING RESPIRATION FROM INTRACARDIAC ELECTROGRAMS (EGM) OR ECG SIGNALS

TECHNICAL FIELD

This disclosure relates generally to implantable medical devices and, in particular, to a method and apparatus for monitoring respiration in a patient using a cardiac electrical signal.

BACKGROUND

Implantable pacemakers, cardiovertor defibrillators (ICDs), and hemodynamic monitors, are examples of implantable medical devices (IMDs) that sense cardiac electrical signals for monitoring a patient's heart rhythm. The cardiac electrical signals are sensed using electrodes positioned in or around the heart. Such electrodes may be transvenous or intracardiac electrodes for sensing EGM signals or placed subcutaneously to sense ECG signals.

Sometimes additional information relating to other physiological signals is desired for monitoring a patient. For example, information relating to the patients blood pressure, respiration, blood oxygen saturation, or patient activity may be desired. Typically, additional sensors and leads are required in order to sense additional physiological signals to derive such information. Additional sensors and other hardware can increase device cost, size and implantation procedure complexity. For example, methods have been proposed for monitoring respiration using a blood pressure signal, air flow, or thoracic impedance. A pressure sensor, a flow sensor or impedance electrodes, however, may be additional sensors that are not included in a particular medical device system. It is desirable to reduce the number of sensors and hardware needed to monitor physiological signals of interest.

DETAILED DESCRIPTION

Figure 1:
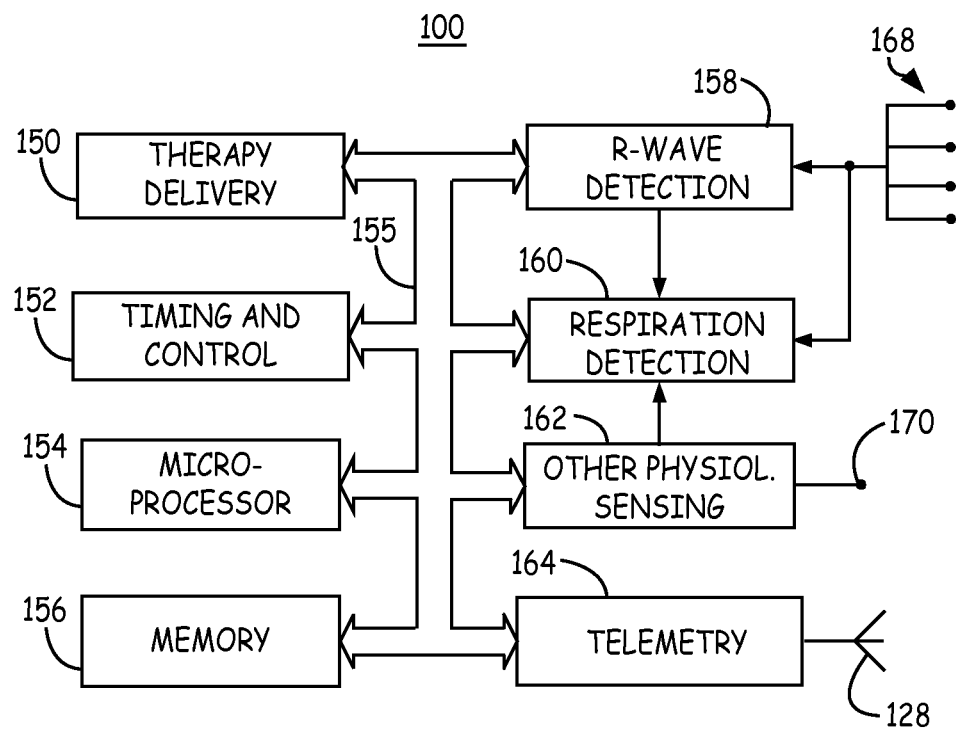
FIG. 1 is a functional block diagram of an IMD for monitoring a patient's respiration using a cardiac electrical signal.

In the following description, references are made to illustrative embodiments. It is understood that other embodiments may be utilized without departing from the scope of the disclosure. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of an IMD for monitoring a patient's respiration using a cardiac electrical signal. IMD 100 generally includes timing and control circuitry 152 and an operating system that may employ microprocessor 154 or a digital state machine for timing sensing and therapy delivery functions in accordance with a programmed operating mode. Microprocessor 154 and associated memory 156 are coupled to the various components of IMD 100 via a data/address bus 155. IMD 100 includes therapy delivery unit 150 for delivering a therapy to the patient. Therapy delivery unit may include a pulse generator for delivering electrical stimulation therapies, such as cardiac pacing therapies, arrhythmia therapies including cardioversion/defibrillation shocks, or nerve stimulation pulses, under the control of timing and control 152. In this case, therapy delivery unit 150 is typically coupled to two or more electrodes, which may be electrodes 168 or other electrodes (not shown), for delivering therapeutic pulses.

Therapy delivery unit 150 may additionally or alternatively include other therapy delivery capabilities, such as a fluid pump for delivering a pharmaceutical or biological agent. In other embodiments, IMD 100 may be provided as a monitoring device without therapy delivery capabilities.

Electrodes 168 are used for receiving electrical signals from the heart. Two or more electrodes may be configured in a unipolar or bipolar sensing configuration for sensing cardiac signals. Electrodes may be carried by a lead for intracardiac, epicardial, transvenous, or subcutaneous or submuscular extrathoracic placement. Electrodes 168 may also include leadless electrodes incorporated along a conductive housing (not shown) of medical device 100 which encloses the circuitry configured to perform the functionality shown in FIG. 1.

Cardiac electrical signals are sensed using any of electrodes 168 for monitoring the patient's heart rhythm. Electrodes 168 are coupled to R-wave detection circuitry 158 for monitoring a ventricular rate. In other embodiments, IMD 100 may additionally or alternatively include P-wave detection circuitry for monitoring an atrial rate. The intervals between sensed R-waves (and/or P-waves) are used by microprocessor 154 in detecting cardiac arrhythmias. When a cardiac arrhythmia is detected a cardiac pacing or shock therapy may be delivered as needed. Electrodes 168 may include designated sensing electrodes and designated therapy delivery electrodes. Alternatively, any of electrodes 168 may be used for both sensing and therapy delivery.

Electrodes 168 are also coupled to respiration detection circuitry 160. Respiration detection circuitry receives EGM or ECG signals, "referred to herein collectively as cardiac signals, for detecting R-wave peaks for generating an R-wave peak waveform. The R-wave peak waveform is used for monitoring respiration as will be described below. Respiration rate, respiration depth, or other respiration metrics may be used by microprocessor for monitoring for breathing disorders, such as sleep apnea or Cheyne-Stokes breathing, or for determining general patient status. Respiration may also be used for controlling other physiological signal monitoring. For example, in order to remove respiration effects or artifact on other physiological signals, a respiration signal derived from a cardiac signal may be used to control sensing of other signals during a selected portion of the respiration cycle, e.g. during expiration only.

IMD 100 may additionally or alternatively be coupled to other physiological sensors 170. Physiological sensors 170 may include a pressure sensor, acoustical sensor, accelerometer, flow sensor, blood chemistry sensor, impedance sensor, blood oxygen saturation sensor, patient activity sensor or other physiological sensors known for use with implantable medical devices. Physiological sensors may be carried by leads extending from IMD 100 or incorporated in or on the IMD housing.

Signals received by sensor(s) 170 are received by signal processing circuitry 162 which provides physiological signals to microprocessor 154 for detecting physiological events or conditions.

The operating system includes associated memory 156 for storing a variety of programmed-in operating mode and parameter values that are used by microprocessor 154. The memory 156 may also be used for storing data compiled from sensed physiological signals and/or relating to device operating history for telemetry out on receipt of a retrieval or interrogation instruction.

IMD 100 further includes telemetry circuitry 164 and antenna 128. Programming commands or data are transmitted during uplink or downlink telemetry between telemetry circuitry 164 and external telemetry circuitry included in a programmer or monitoring unit.

Figure 2:
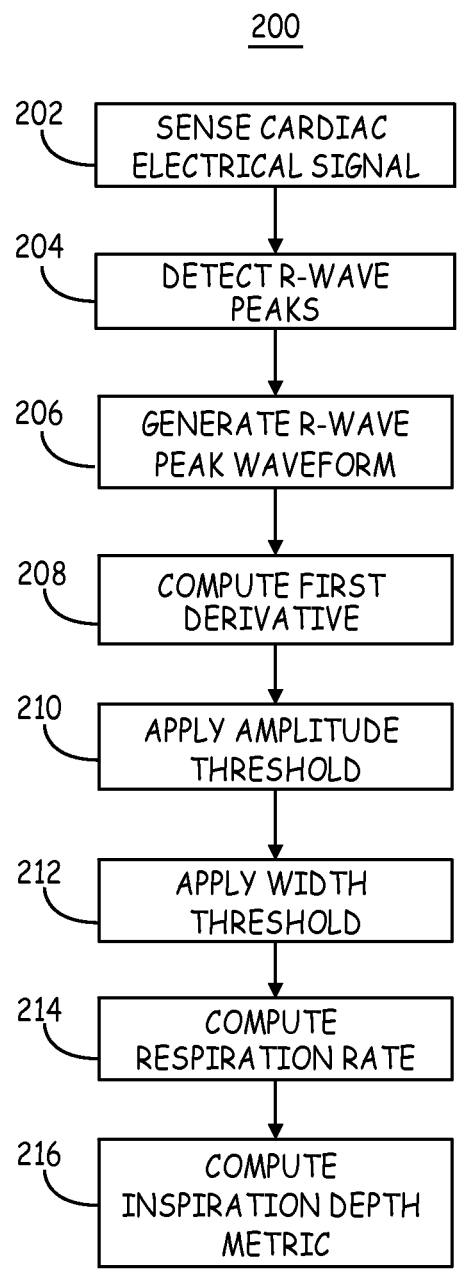
FIG. 2 is a flow chart of one method for monitoring respiration using a cardiac electrical signal.

FIG. 2 is a flow chart of one method for monitoring respiration using a cardiac signal. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a cardiac electrical signal is sensed using electrodes operatively positioned in the vicinity of the patient's heart. As indicated above, intracardiac EGM signals are sensed using electrodes carried by transvenous leads, however, other electrodes and positions may be used for sensing the cardiac electrical activity.

At block 204, R-wave peaks are detected. R-waves are typically sensed using an auto-adjusting sensing threshold with appropriate blanking periods and sensing refractory periods applied. When an R-wave is sensed, a peak detector is used to measure the peak-to-peak amplitude of the R-wave (i.e., the difference between minimum data point value and maximum data point value of the R wave). The peak-to-peak amplitude is used for generating an R-wave peak waveform at block 206. The R-wave peak waveform essentially plots the peak-to-peak amplitude of the R-wave over time.

At block 208, the first derivative of the R-wave peak waveform is computed. An amplitude threshold is applied to the first derivative of the R-wave peak waveform at block 210 to detect cycles of increased R-wave peak amplitude that correspond to the modulation of the cardiac electrical signal due to inspiration and expiration. Both the increasing or positive-going threshold crossing and the decreasing or negative-going threshold crossing are determined to mark a time corresponding to an early portion of the inspiration phase and a time corresponding to a late portion of the inspiration phase, thereby defining an "inspiratory pulse" that can be used to approximate an inspiratory phase of the respiration cycle.

At block 212, a width threshold may additionally be applied to the approximated inspiratory phase. If a positive-going threshold crossing and a negative-going threshold crossing occur within a time interval that is less than the width threshold, the threshold-crossings are rejected as not being associated with an inspiration phase.

Using the inspiratory pulses defined by the positive-going and negative-going threshold crossings, and meeting the width threshold requirement, a respiration rate can be computed at block 214. Additionally, the width of the inspiratory pulses can be used to compute a metric of respiration that is a surrogate for inspiration depth. The width, i.e. the duration, of the inspiration pulse is expected to be closely correlated to inspiration depth.

Figure 3:
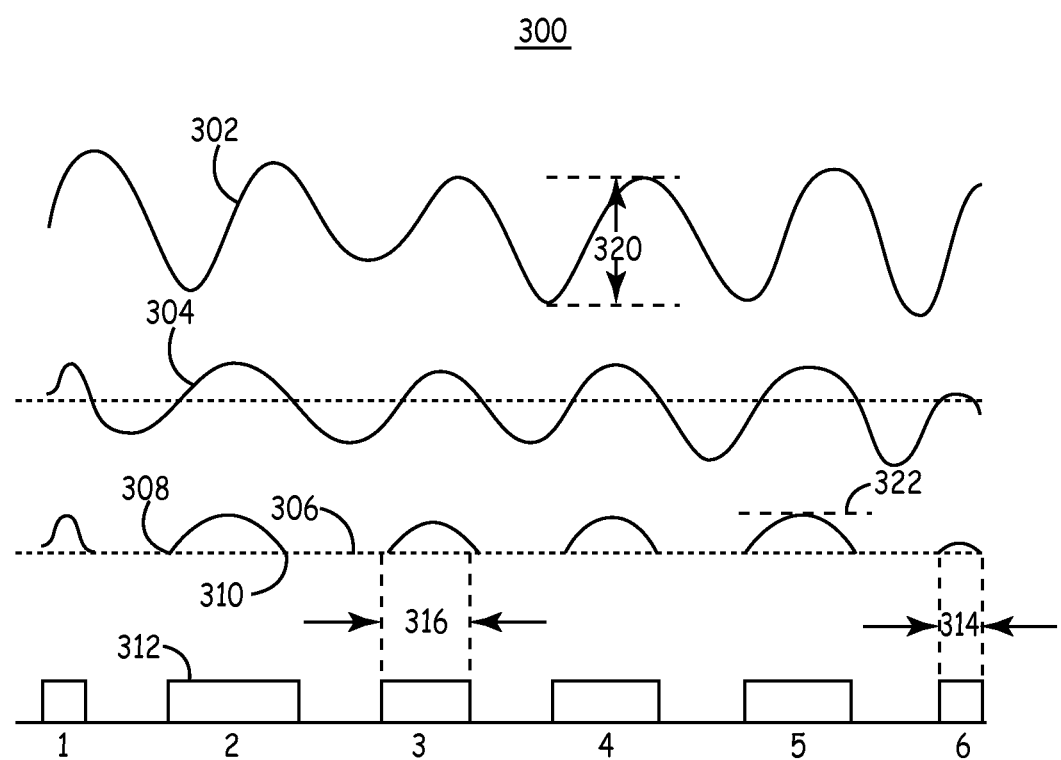
FIG. 3 is a timeline depicting an R-wave peak waveform, the first derivative of the R-wave peak waveform, and inspiration pulses derived from the first derivative of the R-wave peak waveform signal.

FIG. 3 is a timeline 300 depicting an R-wave peak waveform 302, the first derivative of the R-wave peak waveform 304, and respiration pulses 310 derived from the first derivative of the R-wave peak waveform signal. The R-wave peak waveform 302 is a time-based plot of the R-wave peak amplitude detected for each cardiac cycle at block 204 of flow chart 200.

The first derivative signal 304 is the first derivative of the R-wave peak waveform 302. A threshold 306 is applied to the first derivative signal 304 to determine positive-going threshold crossing points 308 and negative-going threshold crossing points 310. An inspiration pulse 312 is defined by a consecutive pair of a positive-going and a negative-going threshold crossing 308 and 310, respectively.

As described above, a width threshold 314 may be applied to each inspiration pulse to reject pulses considered to be too narrow to be associated with an actual respiration cycle and are more likely due to other noise or artifact. In some embodiments, a maximum width may also be defined to reject inspiration pulses deemed too long to be an actual inspiration phase. A long pulse width could occur with postural changes or other artifact that affects R-wave amplitude.

In the example shown 6 inspiration pulses, all meeting the width threshold 314, are detected. The number of pulses may be counted during a preset interval, for example 30 seconds, 60 seconds or another interval, to determine a respiration rate. In alternative embodiments, a timer may be restarted each time an inspiration pulse count reaches a predetermined number and the respiration rate computed from the pulse count and the timer value. Various metrics of respiration rate may be computed such as a maximum, minimum, mean, range or other aspects occurring over a 24 hour period or other predefined interval of time or as associated with patient activity level, heart rate, or other physiological signals.

The duration or width 316 of the inspiration pulses may also be used to assess respiration. A maximum, minimum, range, mean or variability of inspiration pulse width, or other measurements of the pulse widths or any combination thereof, may be determined for assessing the depth and regularity or irregularity of respiration. In this way, various metrics of both rate and width of the inspiration pulses as surrogates for actual respiration rate and respiration depth measurements would allow a variety of patient conditions and breathing disorders to be monitored, including but not limited to sleep apnea, Cheyne-Stokes breathing, shortness of breath associated with heart failure or other conditions, asthma, etc.

Alternatively, inspiration depth may be monitored by measuring the peak-to-peak amplitude difference 322 between a minimum data point and a neighboring maximum data point on the R-wave peak waveform 302, when at least the maximum data point occurs within a respiration pulse 312.

Another respiration metric that can be monitored is the maximum peak value 322 of the first derivative waveform 304. The maximum peaks 322 of the first derivative waveform 304 are expected to be correlated to the abruptness of respiration and may reflect both the respiration depth and the duration of inhalation. A respiration metric computed using the maximum peak value 322 may be correlated to inspiratory flow rate. Trends in the maximum peak value 322 of the first derivative waveform 304 may reflect a patient condition, such as a heart failure condition.

Figure 4:
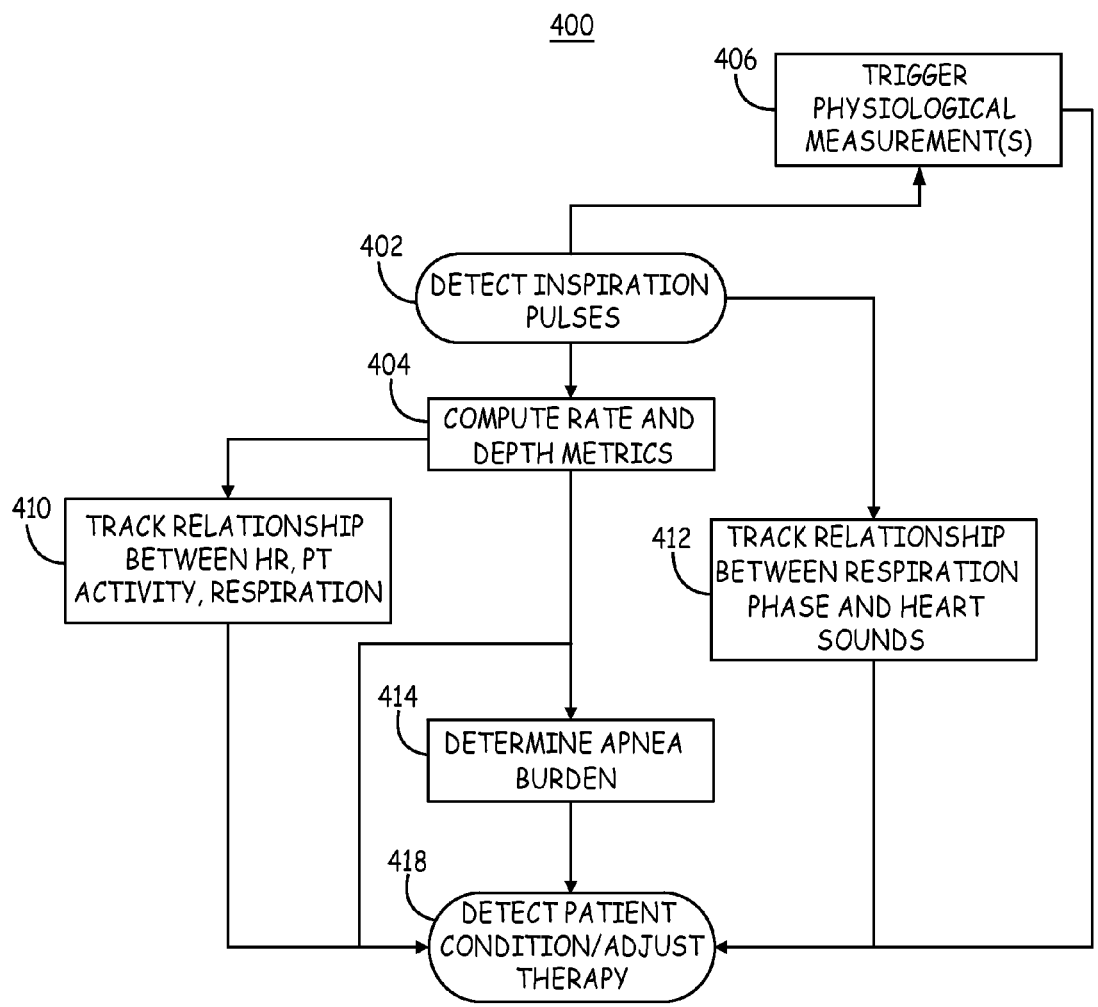
FIG. 4 is a diagram of a monitoring method for utilizing respiration metrics derived from a cardiac electrical signal for assessing or detecting various patient conditions.

FIG. 4 is a diagram 400 of a monitoring method for utilizing respiration metrics derived from a cardiac electrical signal for assessing or detecting various patient conditions. The methods shown in diagram 400 may be combined in an implantable medical device that is at least capable of sensing cardiac electrical signals and may include other physiological signal sensing and/or therapy delivery capabilities. A device may include one or more of the monitoring methods shown in diagram 400 in any combination.

Inspiration pulses are detected according to the methods described above in conjunction with FIGS. 2 and 3 at block 402. The detection of an inspiration phase (or conversely an expiration phase occurring between inspiration pulses) can be used to trigger other physiological measurements that are subject to modulation by respiration. Other measurements, such as blood pressure, heart sounds, impedance, etc. may be triggered at block 406 to occur during the same phase of the respiration cycle in response to inspiration pulse detection. For example, a measurement may be triggered to always occur during the inspiration phase or always during the expiration phase to compensate for respiratory effects on the physiological signal.

The inspiration pulses are used to compute one or more metrics relating to respiration rate and respiration depth at block 404 as described above. The rate and depth metric may be used for monitoring a patient condition in combination with other physiological signals. For example, the relationship between respiration, heart rate and patient activity may be tracked at block 410. The rate that respiration rate and/or depth increases and/or decreases with increasing/decreasing heart rate or activity may be monitored, for example, to assess the status of a heart failure patient.

At 412, the relationship between heart sounds and respiration phase may be tracked. The heart sound S2 is the combination of two sounds, A2 caused by closure of the aortic valve and P2 caused by closure of the pulmonic valve. Normally, A2 and P2 occur within approximately 30 ms of each other during expiration and are perceptually a single sound. During inspiration, however, the separation of A2 and P2 widens to be perceived as two distinct sounds, with A2 occurring earlier than P2. In hypertrophic cardiomyopathy, this relationship of respiratory phase and the S2 heart sounds reverses. A2 and P2 are distinctly separate during expiration with P2 leading A2. During inspiration, the separation of A2 and P2 decreases, and A2 and P2 can merge. As such, the affect of respiration phase on the relationship of heart sounds can be monitored to assess the progression of certain cardiac conditions.

At block 414, apnea burden or the burden of other breathing disorders may be determined based on respiration rate and depth metrics. Breathing disorder burden can be used to track the progression of a disease or condition.

The relationships tracked at block 410, 412, and 414 as well as other physiological measurements from block 406 may be used in detecting a patient condition requiring medical attention or therapeutic intervention. An alarm or alert may be generated at block 418 to notify a patient or medical-caregiver of a detected condition. If the monitoring device is capable of delivering a therapy, the therapy may be adjusted at block 418, which may involve turning a therapy on or off or increasing or decreasing a therapy control parameter. The rate and depth metrics computed at block 404 may be used directly at block 418 in detecting a patient condition and/or controlling a therapy.

Therapies that may be adjusted in response to respiration monitoring shown in diagram 400 include cardiac pacing, cardiac resynchronization therapy (CRT), vagal nerve stimulation, or stimulation of upper airways or continuous positive airway pressure (CPAP) for treating sleep apnea.

Figure 5:
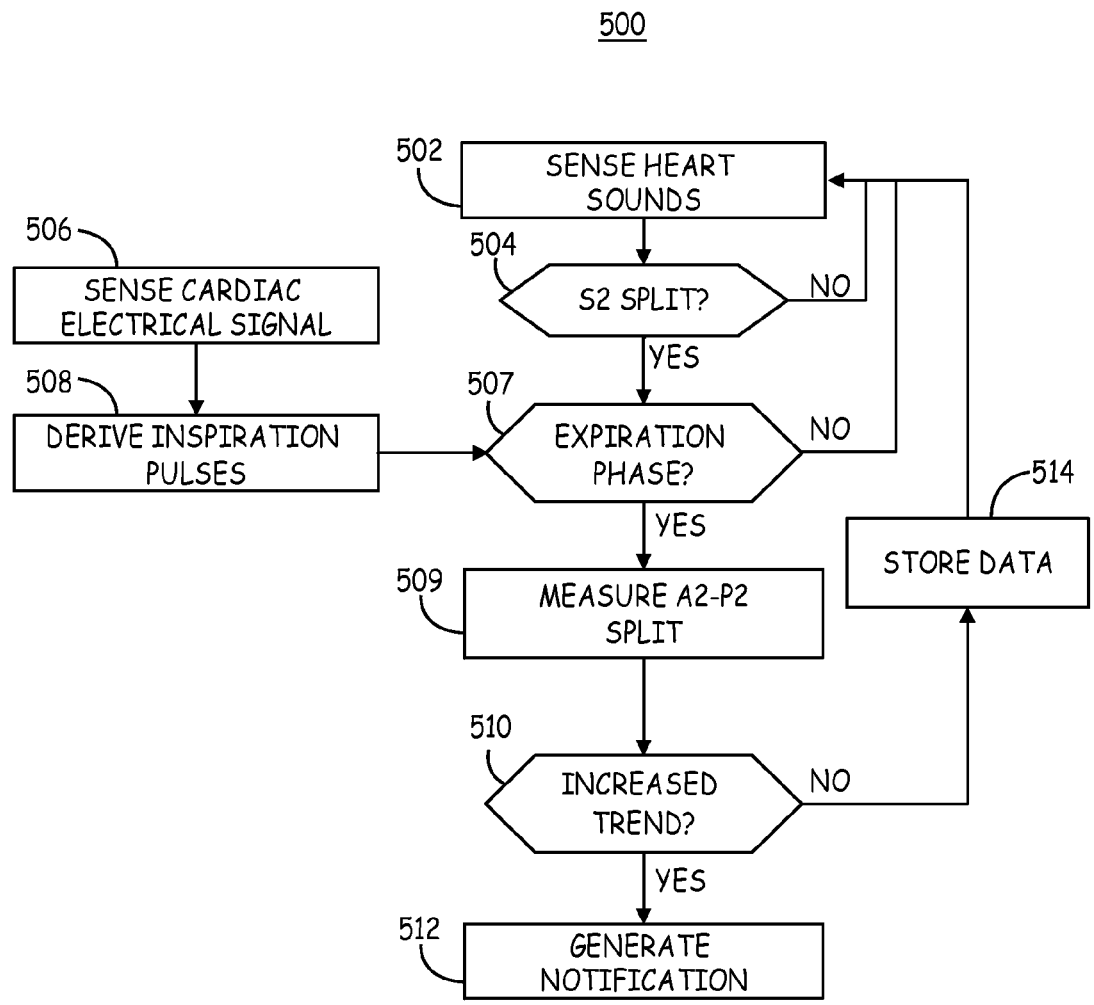
FIG. 5 is a flow chart for monitoring the relationship between heart sounds and respiration phase.

FIG. 5 is a flow chart 500 for monitoring the relationship between heart sounds and respiration phase. At block 502, heart sounds are sensed using an acoustical sensor, such as a microphone or an accelerometer. At block 504, a determination is made whether the second heart sound S2 is split. If there is no splitting of the heart sound S2, the process returns to block 502 to monitor the heart sounds on the next cardiac cycle. It is recognized that sensing of heart sounds may be facilitated by using timing windows set based on sensed R-waves or other fiducial points identified on the EGM or ECG signal.

Concurrently with heart sound sensing, the respiration phase is determined by sensing a cardiac electrical signal at block 506 and deriving inspiration pulses at block 508 according to the method described in conjunction with FIGS. 2 and 3.

If S2 is split, as determined at block 504, the respiration phase is identified at block 507 in response to the inspiration pulses derived from the cardiac electrical signal at block 508. If the current respiration phase is expiration, as determined at block 507, the time interval between the A2 and P2 sounds is measured at block 509. This separation of A2 and P2 sounds during the expiration phase is abnormal and the trend in the splitting interval may be monitored to assess the patient's cardiac condition. If the current respiration phase is not expiration, i.e. inspiration, splitting of the S2 sound is normal and the method returns to block 502 to continue monitoring.

At block 510, the splitting interval measured at block 508 may be compared to one or more preceding intervals to determine if there is an increasing trend in the splitting interval. If so, a notification is generated at block 512 to alert the patient or physician of a worsening cardiac condition.

If an alert condition is not detected at block 510, the splitting interval data may be stored at block 514, and the monitoring process continues by returning to block 502.

Thus, respiration monitoring methods and associated apparatus have been presented in the foregoing description with reference to specific embodiments. It is appreciated that various modifications to the referenced embodiments may be made without departing from the scope of the disclosure as set forth in the following claims.

The invention claimed is:

1. A method for monitoring respiration in a patient, the method comprising:
  sensing a cardiac electrical signal;
  detecting a plurality of signal peaks of the cardiac electrical signal;
  generating, by a respiration detection circuit of a medical device, a peak amplitude waveform in response to the plurality of signal peaks;
  computing a first derivative signal of the peak amplitude waveform;
  deriving, by the respiration detection circuit, inspiration pulses in response to the first derivative signal; and computing a respiration metric in response to the inspiration pulses, wherein deriving inspiration pulses in response to the first derivative signal comprises:
establishing an amplitude threshold;
identifying a positive-going amplitude threshold crossing of the first derivative signal; and
defining an onset of an inspiration pulse of the derived inspiration pulses in response to the positive-going threshold crossing.

2. The method of claim 1, further comprising identifying a negative-going threshold crossing of the first derivative signal following the positive-going threshold crossing, and defining an end of the inspiration pulse in response to the negative-going threshold crossing.

3. The method of claim 2, further comprising:
establishing a width threshold;
comparing the width threshold to an inspiration pulse width defined by the onset and the end of the inspiration pulse; and
rejecting the inspiration pulse in response to the pulse width being less than the width threshold.

4. A method for monitoring respiration in a patient, the method comprising:
sensing a cardiac electrical signal;
detecting a plurality of signal peaks of the cardiac electrical signal;
generating, by a respiration detection circuit of a medical device, a peak amplitude waveform in response to the plurality of signal peaks;
computing a first derivative signal of the peak amplitude waveform;
deriving, by the respiration detection circuit, inspiration pulses in response to the first derivative signal; and
computing a respiration metric in response to the inspiration pulses, wherein computing a respiration metric comprises determining a peak value of the first derivative waveform.

5. A method for monitoring respiration in a patient, the method comprising:
sensing a cardiac electrical signal;
detecting a plurality of signal peaks of the cardiac electrical signal;
generating, by a respiration detection circuit of a medical device, a peak amplitude waveform in response to the plurality of signal peaks;
computing a first derivative signal of the peak amplitude waveform;
deriving, by the respiration detection circuit, inspiration pulses in response to the first derivative signal; and
computing a respiration metric in response to the inspiration pulses, wherein computing a respiration metric comprises computing a metric of inspiration depth using a width of an inspiration pulse of the derived inspiration pulses.

6. The method of claim 5, further comprising measuring a peak-to-peak amplitude difference between a minimum data point and a maximum data point on the peak amplitude waveform when at least the maximum data point occurs within the width of the inspiration pulse.

7. A method for monitoring respiration in a patient, the method comprising:
sensing a cardiac electrical signal;
detecting a plurality of signal peaks of the cardiac electrical signal;
generating, by a respiration detection circuit of a medical device, a peak amplitude waveform in response to the plurality of signal peaks;
computing a first derivative signal of the peak amplitude waveform;
deriving, by the respiration detection circuit, inspiration pulses in response to the first derivative signal; and
computing a respiration metric in response to the inspiration pulses, further comprising determining a relationship between one of a rate and a width of an inspiration pulse of the inspiration pulses and one of a heart rate and a patient activity.

8. A device for monitoring respiration in a patient, comprising:
a cardiac electrode pair to sense a cardiac electrical signal;
a peak detecting circuit to detect a plurality of signal peaks of the cardiac electrical signal;
a processor configured to generate a peak amplitude waveform in response to the plurality of signal peaks, compute a first derivative signal of the peak amplitude waveform, derive inspiration pulses in response to the first derivative signal, and compute a respiration metric in response to the inspiration pulses; and
a memory storing an amplitude threshold, wherein the processor is configured to identify a positive-going amplitude threshold crossing of the first derivative signal, and define an onset of an inspiration pulse of the derived inspiration pulses in response to the positive-going threshold crossing.

9. The device of claim 8, wherein the processor is further configured to identify a negative-going amplitude threshold crossing of the first derivative signal following the positive-going threshold crossing, and define an end of the inspiration pulse in response to the negative-going threshold crossing.

10. The device of claim 9, wherein the memory stores a width threshold, and wherein the processor is configured to compare the width threshold to an inspiration pulse width defined by the onset and the end of the inspiration pulse, and reject the inspiration pulse in response to the pulse width being less than the width threshold.

11. A device for monitoring respiration in a patient, comprising:
a cardiac electrode pair to sense a cardiac electrical signal;
a peak detecting circuit to detect a plurality of signal peaks of the cardiac electrical signal; and
a processor configured to generate a peak amplitude waveform in response to the plurality of signal peaks, compute a first derivative signal of the peak amplitude waveform, derive inspiration pulses in response to the first derivative signal, and compute a respiration metric in response to the inspiration pulses, wherein the processor is configured to determine a peak value of the first derivative waveform for computing a respiration metric.

12. A device for monitoring respiration in a patient, comprising:
a cardiac electrode pair to sense a cardiac electrical signal;
a peak detecting circuit to detect a plurality of signal peaks of the cardiac electrical signal; and
a processor configured to generate a peak amplitude waveform in response to the plurality of signal peaks, compute a first derivative signal of the peak amplitude waveform, derive inspiration pulses in response to the first derivative signal, and compute a respiration metric in response to the inspiration pulses, wherein the processor is configured to compute a metric of inspiration depth using a width of an inspiration pulse.

13. The method of claim 12, wherein the processor is further configured to measure a peak-to-peak amplitude difference between a minimum data point and a maximum data point on the peak amplitude waveform when at least the maximum data point occurs within the width of an inspiration pulse of the derived inspiration pulses.

14. A device for monitoring respiration in a patient, comprising:

a cardiac electrode pair to sense a cardiac electrical signal;

a peak detecting circuit to detect a plurality of signal peaks of the cardiac electrical signal; and a processor configured to generate a peak amplitude waveform in response to the plurality of signal peaks, compute a first derivative signal of the peak amplitude waveform, derive inspiration pulses in response to the first derivative signal, and compute a respiration metric in response to the inspiration pulses, wherein the processor is configured to determine a relationship between one of a rate and a width of an inspiration pulse of the derived inspiration pulses and one of a heart rate and a patient activity.

* * * * *